United States Patent [19]

Heller et al.

[11] Patent Number: 5,955,005
[45] Date of Patent: Sep. 21, 1999

[54] AQUEOUS DISPERSIONS AND THEIR USE FOR TREATING TEXTILES

[75] Inventors: Jürg Heller, Oberwil, Switzerland; Jean-Luc Mura, Rixheim, France

[73] Assignee: Clariant Finance (BVI) Limited, Tortola, Virgin Islands (Br.)

[21] Appl. No.: 08/899,264

[22] Filed: Jul. 23, 1997

[30] Foreign Application Priority Data

Jul. 22, 1996 [GB] United Kingdom ............. 9615354

[51] Int. Cl.[6] .......................... D06M 13/12; F21V 9/06
[52] U.S. Cl. ........................ 252/589; 8/115.56; 8/442; 8/607; 252/8.61; 252/8.81; 252/8.91; 568/333
[58] Field of Search .................. 252/8.61, 8.81, 252/8.91, 589; 8/115.56, 442, 607; 568/333

[56] References Cited

U.S. PATENT DOCUMENTS

| | | | |
|---|---|---|---|
| 3,322,705 | 5/1967 | Kauder et al. | 260/23 |
| 3,580,927 | 5/1971 | Wear | 260/333 |
| 4,631,066 | 12/1986 | Minemura et al. | 8/115.56 |
| 5,498,345 | 3/1996 | Jollenbeck et al. | 252/589 |

FOREIGN PATENT DOCUMENTS 0 490 819 A1  6/1992  European Pat. Off. .

OTHER PUBLICATIONS

Derwent abstract of Japanese 58157881 (Sep. 1983).
Chemical Abstracts vol. 88, 1978 137415 abstract of Japanese Patent specification No. 52–093462 (Aug. 1977).
European Search Report (Oct 1977).

*Primary Examiner*—Anthony Green
*Attorney, Agent, or Firm*—Scott E. Hanf

[57] ABSTRACT

An aqueous dispersion comprising at least one of the UV absorbing compounds of the following formulae I, II or III as below defined: A—B (I); A—C—A (II); or B—A—B (III); wherein in Formula (I) and (II)

A = 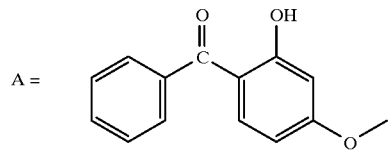

and in Formula III, A is

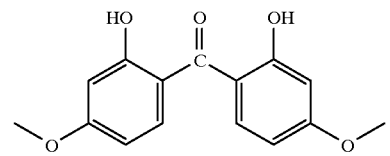

B =

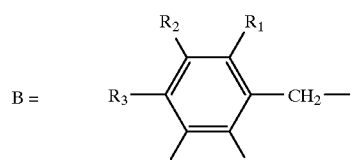

C = 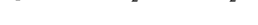 and

Y being a direct bond, a substitute $C_{1-4}$ alkylene group,

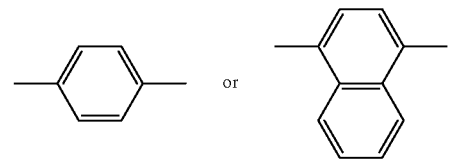

and $R_1$ to $R_5$ independently of each other are hydrogen; $C_{4-4}$ alkyl, the alkyl optionally being substituted; aryl; heterocyclyl; or any two of $R_1$ to $R_5$ which are adjacent, together form part of a ring, with the proviso that no more than four of $R_1$ to $R_5$ are hydrogen.

13 Claims, No Drawings

AQUEOUS DISPERSIONS AND THEIR USE FOR TREATING TEXTILES

The present invention relates to a method of treating a textile with an aqueous dispersion comprising at least one UV absorbing compound selected from a specified group of UV absorbing compounds, in order to improve the light fastness of the thus treated textile, to an aqueous dispersion of said compounds, to use of the UV absorbing compounds for textile treatment and to a number of novel UV absorbing compounds which are members of said group.

It is known to treat textiles with an aqueous dispersion of a specific UV absorbing compound in order to improve the light fastness of the thus treated textile. The object of the present invention is to provide further aqueous dispersions of a UV absorbing compound which are suitable for treating textiles in order to improve the light fastness of the thus treated textiles. The aqueous dispersions according to the present invention have not previously been disclosed in the form of an aqueous dispersion. Furthermore a number of the compounds suitable for use in the present invention, have not previously been known.

The present invention accordingly provides an aqueous dispersion comprising at least one of the UV absorbing compounds of the following formulae I, II or III as below defined:

A—B (I); A—C—A (II); or B—A—B (III); wherein in Formula (I) and (II)

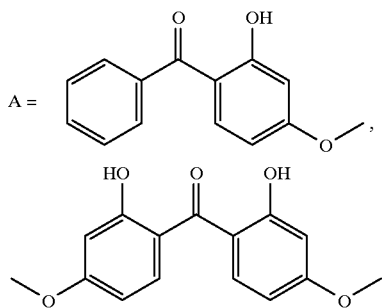

and in Formula (III), A is

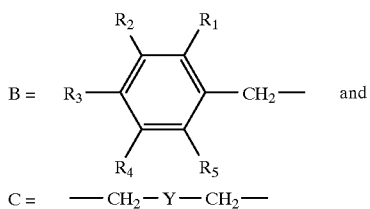

C = —CH$_2$—Y—CH$_2$—

Y being a direct bond, a substituted C$_{1-4}$ alkylene group,

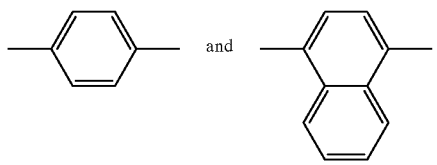

and

R$_1$ to R$_5$ independently of each other are hydrogen, C$_{1-4}$ alkyl, the alkyl optionally being substituted, aryl, heterocy-clyl or any two of R$_1$ to R$_5$ which are adjacent, together form part of a ring, with the proviso that no more than four of R$_1$ to R$_5$ are hydrogen.

Preferred compounds are of formula I or II. Most preferred compound are those of formula II in which Y is a C$_{1-4}$ alkylene group substituted by a hydroxy group or phenylene.

In a further embodiment of the present invention, there is provided a process for improving the light fastness of a textile material characterized in that the material is treated with an aqueous dispersion comprising at least one of the compounds of formula (I), (II) or (III) as above defined, the treatment with the aqueous dispersion being before, during or after a long or short bath, an exhaust or slop-padding dyeing process or a printing process.

The present invention further provides use of the aqueous dispersions of the invention for treatment of a textile material in order to improve the light fastness of the thus textile material.

The materials which are suitable for treatment according to the process of the present invention, are textile materials which are in the form of fibers, threads or materials produced therefrom, which may for example be woven or knitted. The textile materials may be any fully- or semi-synthetic or natural material, mixtures of either synthetic or natural materials or mixtures of both synthetic and natural materials such as for example polyester-cotton mixtures. It has been found that the dispersions of the present invention show particularly good results when used for the treatment of polyester textile materials. The textile materials of the present invention, namely those which have been treated with an aqueous dispersion of the present invention are particularly useful for use as automobile upholstery. Due to the high sublimation fastness of the compounds used in the aqueous dispersions and processes of the present invention, sublimation of the compounds under high temperatures, as are commonly experienced inside an automobile which is left in direct sunshine, either does not occur or occurs only to a minimal extent, that is the compounds can be described as being sublimation stable. The sublimation stability can be shown by thermo-gravimetric analysis. This sublimation stability is an important advantage in the automobile industry since a compound which is stable to sublimation does not sublime or sublimes to a very low extent and accordingly one does not observe the fogging of the car wind screen which occurs with compounds which sublime.

The aqueous dispersions of the present invention are applied to the material to be treated before, during or after a long or short bath, an exhaust or slop-padding dyeing process or printing process. The long or short bath, the exhaust or slop-padding dyeing process or printing process used in the process of the present invention are all conventional processes.

Fixing of the UV absorbing compound to the textile material is similarly effected in a conventional manner, such as by thermo-fixation. Fixing may occur during the dyeing process for example during exhaust dyeing or it may take place subsequent to the dyeing or printing process by means of a conventional heating step. A typical temperature at which fixing may be carried out is at about 180° C. for a period of about 1 minute. For security belts, the fixing temperature is about 210° C. for a period of about 6 to 8 minutes.

It is particularly advantageous if the aqueous dispersions of the present invention are present during the dyeing process, that is they are added to the dye bath. Accordingly in a preferred embodiment of the process according to the present invention there is provided a process for improving the light fastness of a textile material characterized in that the material is treated with an aqueous dispersion comprising at least one of the compounds of formula (I), (II) or (III) as above defined, the treatment with the aqueous dispersion being during the dyeing process.

The compounds which are employed in the aqueous dispersions of the present invention all exhibit a high level of sublimation fastness. This property is particularly important in that it allows the compounds to be fixed by means of thermo-fixation without adversely effecting the properties of the compound. Furthermore the compounds used in the aqueous dispersions of the present invention, demonstrate very good exhaustion and are therefore particularly suitable for treating textiles according to the exhaust or slop or padding dyeing processes.

The compounds of formulae I, II or III may be employed in admixture with other UV absorbing compounds which can be formed into an aqueous dispersion. Accordingly in a further embodiment of the present invention there is provided an aqueous dispersion comprising at least one of the compounds of formulae I, II or III and a further water-dispersible UV absorber. Preferably, such UV absorbers are sublimation fast and can be selected from the group of o-hydroxyphenylbenzotriazoles, o-hydroxyphenyltriazines and benzoxazin-4-ones.

The compounds of the present invention are generally employed in quantities of 0.05 to 5.0%, preferably 0.1 to 3.5% and more preferably 0.2 to 3.0%, the percentages being based on the dry weight of the textile material to be treated.

Textile materials which have been treated with an aqueous dispersion of the present invention are also an embodiment of the present invention. In addition to possessing the advantage of having been treated with a UV absorber which displays sublimation stability, as above discussed, and accordingly being particularly of interest to the automobile upholstery industry, such textiles also offer the advantage of comprising a UV absorbing compound and accordingly are suitable for use in the manufacture of clothes. Clothing manufactured utilizing the textiles of the present invention protect the wearer against the harmful UV radiation from the sun. Accordingly in a yet further embodiment of the present invention, there is provided a process for improving the protection afforded a wearer of clothes manufactured from a textile material according to the invention, against the harmful UV radiation from the sun.

The compounds which are used in the present invention may be prepared as shown in the following examples. From the following examples, Examples 6 (Formula I.1), Example 8 (Formula I.2) and Example 9 (Formula I.3) are new compounds.

Accordingly, the present invention further provides a compound of the following formula (Ia):

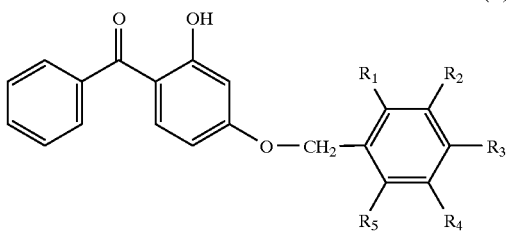

in which $R_1$ to $R_5$ have the meanings given above for formula (I).

A further object of the invention is the use of compounds of formulae I, II and III for stabilizing polymers in the mass.

In the following examples temperatures are given in degrees Celsius.

EXAMPLE 1

42.8 g 2,4-Dihydroxybenzophenone and 17.5 gα, α'-dichloro-m-xylene are dissolved in 250 ml ethanol. To the clear yellowish solution 20 ml of a 30% caustic soda solution are added. The solution is heated to boiling point and kept at reflux for 24 hours. The mixture is cooled to room temperature and then filtered. The product is washed twice with cold ethanol, then with water and dried at 70° C. at reduced pressure to yield 42.2 g (79% of theory) of a yellowish powder, which after recrystallization from chlorobenzene had a melting point of 175–178° C. and a microanalysis corresponding to $C_{34}H_{26}O_6$.

The compound of Example 1 has the following formula:

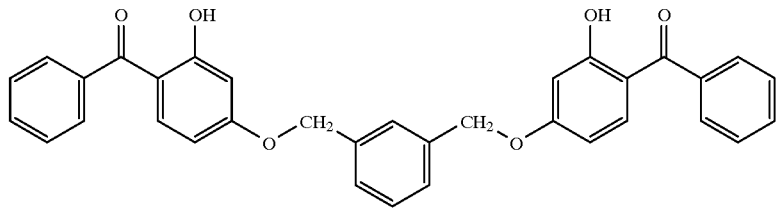

Absorption maxima in dichloromethane solution: 288 nm /ε=44·10³; 326 nm /ε=28·10³.

EXAMPLES 2–5

Similarly the following products are formed by substituting the α, α'-dichloro-m-xylene by:

|  |  |  | mp. | $\lambda_{max}/\epsilon$ |
|---|---|---|---|---|
| Ex. 2: | 17.5 g | α,α'-dichloro-p-xylene | 217–218° C. |  |
| Ex. 3: | 18.8 g | 1,2-dibromo-ethane | 215–216° C. | 288/42 · 10³ |
|  |  |  |  | 328/28 · 10³ |
| Ex. 4: | 12.9 g | 1,3-dichloro-2-propanol | 152–153° C. | 288/42 · 10³ |
|  |  |  |  | 326/27 · 10³ |
| EX. 5: | 22.5 g | 1,4-dichloromethyl-naphthalene | 140–148° C. |  |

The compound of Example 2 has the following formula:

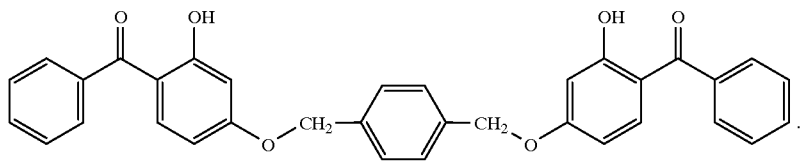

The compound of Example 3 has the following formula:

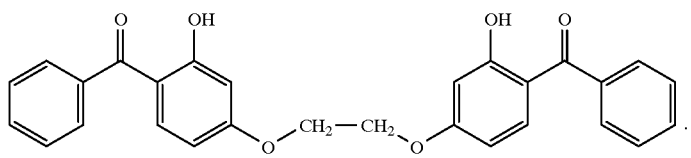

The compound of Example 4 has the following formula:

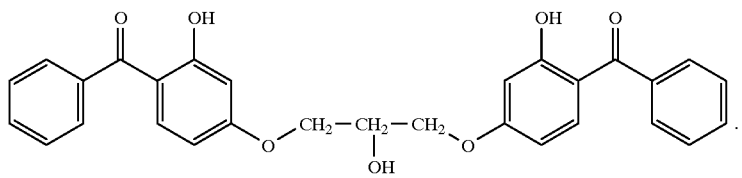

The compound of Example 5 has the following formula:

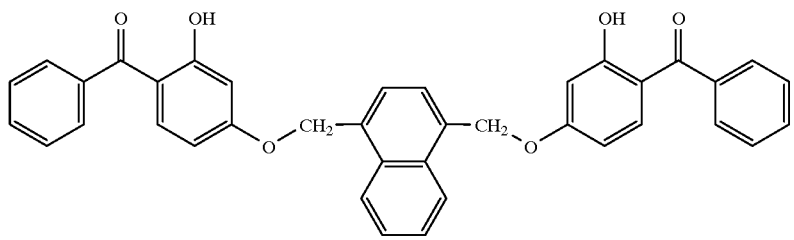

EXAMPLE 6

42.8 g 2,4-Dihydroxybenzophenone and 30.1 g α-chloromethyl-naphthalene are dissolved in 250 ml ethanol. 20 ml of a 30% caustic soda solution are added, and the clear yellow solution is then heated at reflux for 24 hours. The mixture is cooled to 5° C. The precipitate is filtered, washed with cold ethanol, then with water and dried in the vacuum at 60° C. to yield 56.2 g (79% of theory) of a yellow product, which after recrystallization from isopropylalcohol had a melting point of 115–120° C. and a microanalysis corresponding to $C_{24}H_{18}O_3$. Absorption maxima in dichloromethane solution: 290 nm / $\epsilon=31 \cdot 10^3$; 326/$\epsilon=16 \cdot 10^3$.

The compound of Example 6 has the following formula:

(I.1)

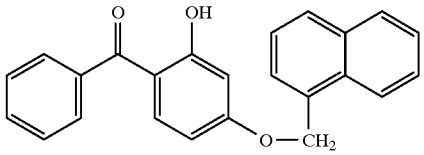

EXAMPLES 7–9

Similarly the following products may be prepared by substituting the α-chloromethyl-naphthalene by:

|  |  |  | mp. | $\lambda_{max}/\epsilon$ |
|---|---|---|---|---|
| Ex. 7: | 48.7 g | Chlorobenzyl-oxazolidine | 186–188° C. |  |
| Ex. 8: | 37.0 g | α-Bromo-p-xylene | 140–142° C. | 288/23 · 10³ |
|  |  |  |  | 326/15 · 10³ |
| Ex. 9: | 31.3 g | 4-Methoxy-benzylchloride | 129–130° C. | 288/24 · 10³ |
|  |  |  |  | 326/15 · 10³ |

The compound of Example 8 has the following formula:

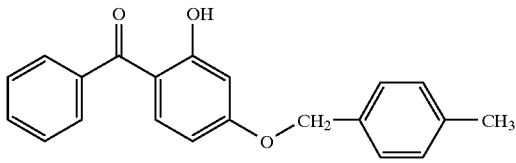

(I.2)

The compound of Example 9 has the following formula:

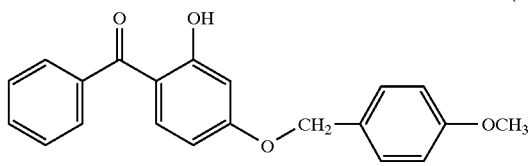

(I.3)

EXAMPLE 10

Synthesis of 2,2'-dihydroxy-4,4'-dibenzyloxybenzophenone 12.3 parts of 2, 2',4,4'-tetrahydroxybenzophenone are dissolved in 150 parts absolute ethanol. After adding 7 parts potassium carbonate and 17.1 parts benzyl bromide, the mixture is heated on reflux overnight. After cooling to room temperature the crystals are filtered off and washed with 300 parts ethanol and dried. The compound of Example 10 has the following formula:

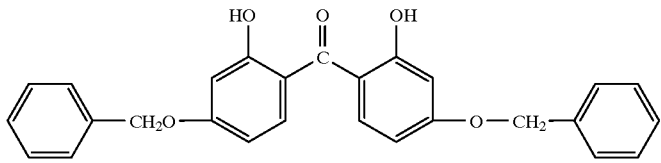

Yield: 19.8 parts (92.5% of theory).
Melting point: 140–142° C.
UV Data: 288 nm=14000 1/mole.cm
354 nm=19700 1/mole.cm

EXAMPLES 11 AND 11a

Production of a Dispersion Preparation 5 parts of the compound of Example 4 are ground for 3 hours in the presence of 2 parts of an oleylalcohol/ethylene oxide dispersant, 93 parts water and 150 parts glass pearls, in a suitable dispersant apparatus. This results in particles having a mean particle size of less than 5 microns. The particles can be separated from the glass pearls by filtration.

20 parts of the compound of example 4 are ground for 3 hours in the presence of 12 parts of formaldehyde condensation product of sulfonated ditolylether, 1.6 part of a triblock copolymer based on polyethylene oxide and polypropylene oxide, 0.8 part of sodium diisooctylsulfosuccinate, 0.2 part of a commercially available biocide, 65.2 parts of water and 150 parts of glass pearls, in a suitable dispersant apparatus. This results in particles having a mean particle size of less than 5 microns. The particles are separated from the glass pearls by filtration, and the pH of the dispersion is adjusted to 6.5 with phosphoric acid. This dispersion is storage stable for one month at 0 and 50° C.

EXAMPLE 12

Carrying Out Of A Light-Stabilized Dyeing 50 parts of (Tersuisse) Polyester-Tricot material are added to a 1000 parts of a dyebath in a HT-dyeing apparatus which contains:
0.8 parts C.I. Disperse Yellow 42; 0.135 parts C.I. Disperse Red 202; 0.315 parts C.I. Disperse Red 86; 5.0 parts of the dispersion of Example 11 above; and 2.0 parts ammonium sulphate.

The pH of the bath is set at 4.5. The material is treated for 5 minutes at a temperature of 60°, thereafter the temperature is brought to 130 over a period of ca. 30 minutes and dyeing is carried out for 60 minutes. After cooling to 60°, the dyed material is removed from the bath, washed and cleaned in a conventional manner with an alkaline solution of sodium hydrosulfite, washed with warm water, neutralized with acetic acid, centrifuged and the residual moisture is removed by air-drying.

EXAMPLE 13

Carrying Out Of A Light-Stabilized Dyeing

Example 12 above is repeated using a goods to liquor ratio of 1:10, the water having a German Hardness of 11° d and a dye bath comprising:
0.19 % C.I. Disperse Yellow 86; 0.185 % C.I. Disperse Yellow 42; 0.122 % C.I. Disperse Red 91; 0.05 % C.I. Disperse Blue 56; 0.44 % C.I. Disperse Blue 77; and 3.5 % of the dispersion of the dispersion of Example 11 above.

EXAMPLE 14

Light Stability Of Polyester Fibers Stabilized With UV Absorbers In The Mass

The tests are performed with a fiber grade polyester, semidull (0.5% TiO₂). The polymer is melt homogenized with stabilizers and then spun to 154 dtex fibers (28 flaments).The processing temperatures are 275–285° C.

The prepared fibers are stretched in a 3.8:1 ratio at 147°. The fibers are wrapped onto card board specimen holders and exposed to accelerated weathering test in an Atlas Weatherometer under conditions according to DIN 53 387 -E.

The degradation of the polymer is monitored by development of yellowness (expressed as b*-CIELAB coordinates; higher values indicate increased yellowing). After 700 hours of accelerated weathering exposure the PET fibers stabilized with 0.5% of the compound according to Example 4 give b*=4.6 compared to b*=5.2 for PET fibers containing 0.5% of the benzotriazole UV absorber Tinuvin 234 (common product for use in this polymer).

We claim:

1. An aqueous dispersion comprising at least one of the UV absorbing compounds of the following formulae I, II or III as below defined:

A—B (I); A—C—A (II); or B—A—B (III); wherein in Formula (I) and (II)

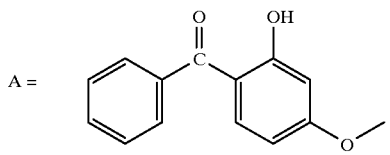

and in Formula (III), A is

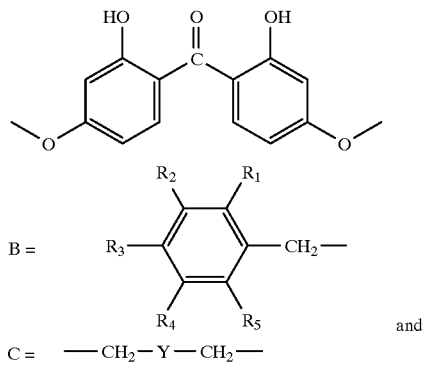

Y being a direct bond, a substituted $C_{1-4}$ alkylene group,

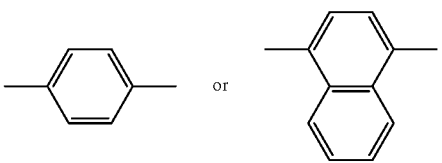

and $R_1$ to $R_5$ independently of each other are hydrogen; $C_{1-4}$ alkyl, the alkyl optionally being substituted; aryl; heterocyclyl; or any two of $R_1$ to $R_5$, which are adjacent, together form part of a ring, with the proviso that no more than four of $R_1$ to $R_5$ are hydrogen.

2. An aqueous dispersion as claimed in claim 1 further comprising an additional water-dispersible UV absorber.

3. An aqueous dispersion as claimed in claim 2 wherein said additional water-dispersible UV absorber is selected from the group consisting of: o-hydroxyphenylbenzotriazoles, o-hydroxyphenyltriazoles, and benzoxazin-4-ones.

4. An aqueous dispersion comprising at least one of the UV absorbing compounds of the following formulae:

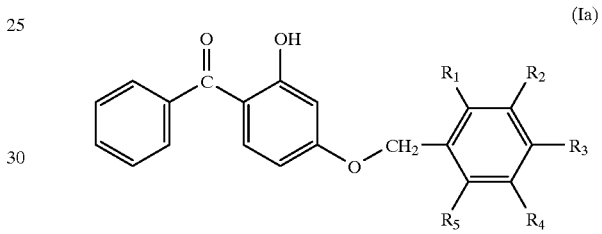

(Ia)

in which $R_1$ to $R_5$ independently of each other are hydrogen; $C_{1-4}$ alkyl, the alkyl optionally being substituted; aryl; heterocyclyl; or any two of $R_1$ to $R_5$, which are adjacent, together form part of a ring, with the proviso that no more than four of $R_1$ to $R_5$ are hydrogen.

5. A process for improving the light fastness of a textile material where said textile material is treated with an aqueous dispersion as claimed in claim 1, the treatment with the aqueous dispersion being applied with a process selected from the group consisting of a dye bath; exhaust dyeing; slop-padding dyeing; and printing.

6. A process as claimed in claim 5, wherein the aqueous dispersion comprises a compound having the formula indicated for any one of the following:

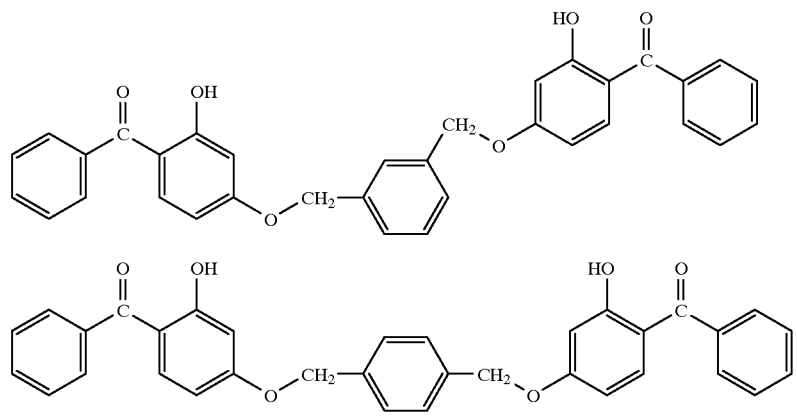

-continued

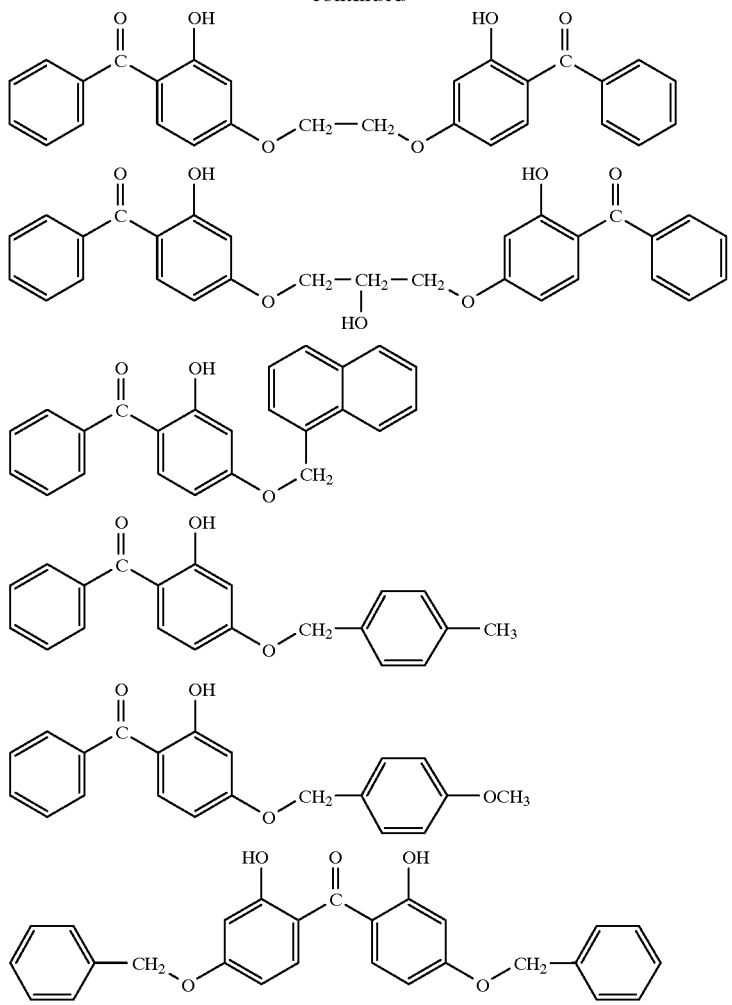

7. A process as claimed in claim 6 wherein the compound is employed in quantities of 0.05 to 5.0%, the percentages being based on dry weight of the textile material to be treated.

8. The process of claim 5 wherein the treatment with the aqueous dispersion is with a dye bath.

9. The process of claim 8 wherein the treatment with the aqueous dispersion is before said dye bath.

10. The process of claim 8 wherein the treatment with the aqueous dispersion is during said dye bath.

11. The process of claim 8 wherein the treatment with the aqueous dispersion is after said dye bath.

12. A process for improving the light fastness of a textile material comprising the steps of:
   providing a textile material;
   contacting said textile material with an aqueous dispersion as claimed in claim 1.

13. A treated textile material produced by the steps of:
   providing a textile material; and
   applying the aqueous dispersion as claimed in claim 1 to said textile material.

* * * * *